US00PP28951P3

(12) United States Plant Patent
Madsen

(10) Patent No.: US PP28,951 P3
(45) Date of Patent: Feb. 6, 2018

(54) ***CAMPANULA* PLANT NAMED 'PKM05'**

(50) Latin Name: ***Campanula* hybrid**
Varietal Denomination: PKM05

(71) Applicant: Gartneriet PKM A/S, Odense N (DK)

(72) Inventor: Christian Hald Madsen, Korsør (DK)

(73) Assignee: Gartneriet PKM A/S, Odense N (DK)

( * ) Notice: Subject to any disclaimer, the term of this patent is extended or adjusted under 35 U.S.C. 154(b) by 45 days.

(21) Appl. No.: 14/756,951

(22) Filed: Nov. 2, 2015

(65) Prior Publication Data

US 2017/0127598 P1 May 4, 2017

(51) Int. Cl.
*A01H 5/02* (2006.01)

(52) U.S. Cl.
USPC ..... Plt./414

(58) Field of Classification Search
USPC ..... Plt./414
See application file for complete search history.

(56) References Cited

PUBLICATIONS

Printout of application information from PLUTO Plant Variety Database for corresponding Canadian application No. 15-8741 filed Nov. 3, 2015 (1 page) (http://www.wipo.int/pluto).
Printout of application information from PLUTO Plant Variety Database for corresponding CPVO application No. 2015/2170 filed Sep. 16, 2015 (1 page) (http://www.wipo.int/pluto).

*Primary Examiner* — Keith O. Robinson
(74) *Attorney, Agent, or Firm* — Foley & Lardner LLP

(57) ABSTRACT

A new and distinct cultivar of *Campanula* plant named 'PKM05', characterized by its compact plant habit; globular plant form; vigorous growth habit; double white flowers and small leaves.

5 Drawing Sheets

Latin name of genus and species of the plant claimed: *Campanula* hybrid.

Variety denomination: 'PKM05'.

BACKGROUND OF THE INVENTION

The present invention relates to a new and distinct cultivar of *Campanula* hybrid plant, and hereinafter referred to by the name 'PKM05'.

The new *Campanula*, 'PKM05', is a product of a planned breeding program conducted by the inventor, Christian Hald Madsen, in Søhus, Denmark. The new *Campanula* originated from a planned cross between two different *Campanula* species; the female parent being an unnamed, proprietary *Campanula* variety (unpatented) and the male parent being an unnamed, proprietary *Campanula* variety (unpatented). The initial crossing was performed in May 2013 by the Inventor, followed by further testing after vegetative propagation since then. The inventor selected 'PKM05' on the basis of white double flowers.

Asexual reproduction of the new *Campanula* cultivar by terminal cuttings has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKM05'. These characteristics in combination distinguish 'PKM05' as a new and distinct cultivar:

1. Upright plant habit with stiff stems.
2. Bushy globular plant form.
3. Vigorous growth habit, but still needing less chemical growth retardation.
4. Double white flowers.
5. No need for vernalization.

Plants of the cultivar 'PKM05' can be compared to the unpatented cultivar *Campanula×haydlodgensis* 'White Wonder'. In side-by-side comparisons conducted by the inventor in Søhus, Denmark, plants of the instant cultivar 'PKM05' and plants of the cultivar 'White Wonder' differ in the following characteristics:

1. Plants of 'PKM05' have larger flowers than 'White Wonder'.
2. Plants of 'PKM05' have larger leaves than 'White Wonder'.
3. Plants of 'PKM05' have a more upright plant habit than 'White Wonder'.

Data on plants of the parent varieties are no longer available for comparison with plants of the new cultivar *Campanula* 'PKM05'.

BRIEF DESCRIPTION OF THE PHOTOGRAPHS

The accompanying colored photographs illustrate the overall appearance of the new *Campanula* 'PKM05', showing the colors as true as it is reasonably possible to obtain in colored reproductions of this type. Colors in the photographs may differ slightly from the color values cited in the detailed botanical description, which more accurately describe the actual colors of 'PKM05'. Plants in the photographs are shown 3 months after propagation.

Figure 1:
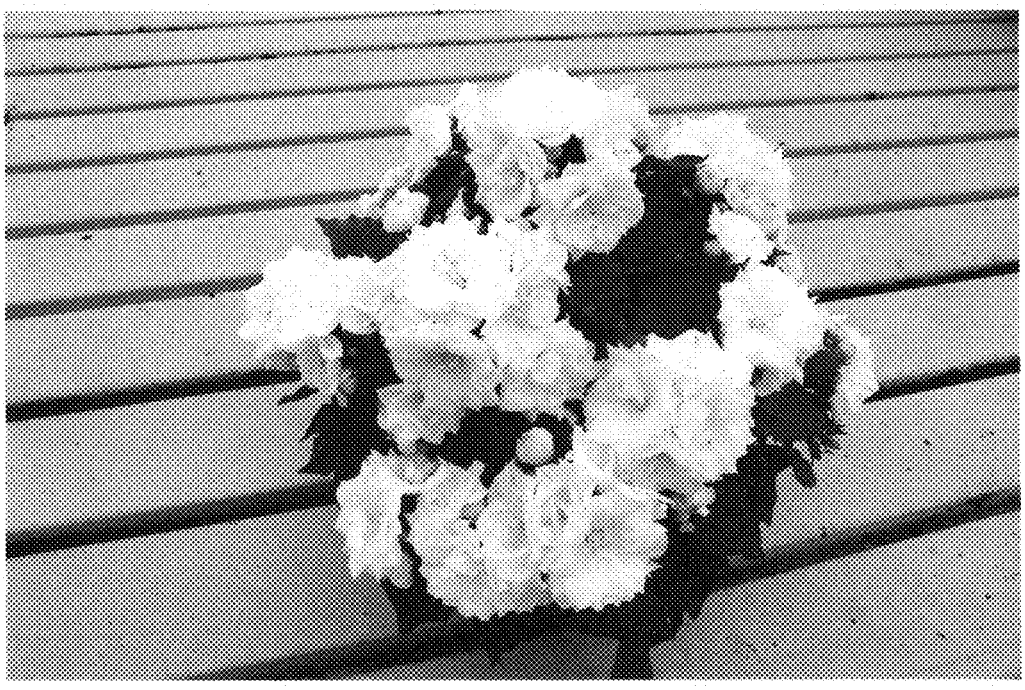

FIG. 1 comprises a side perspective view of a typical flowering plant of 'PKM05' grown in a 10.5 cm pot.

Figure 2:
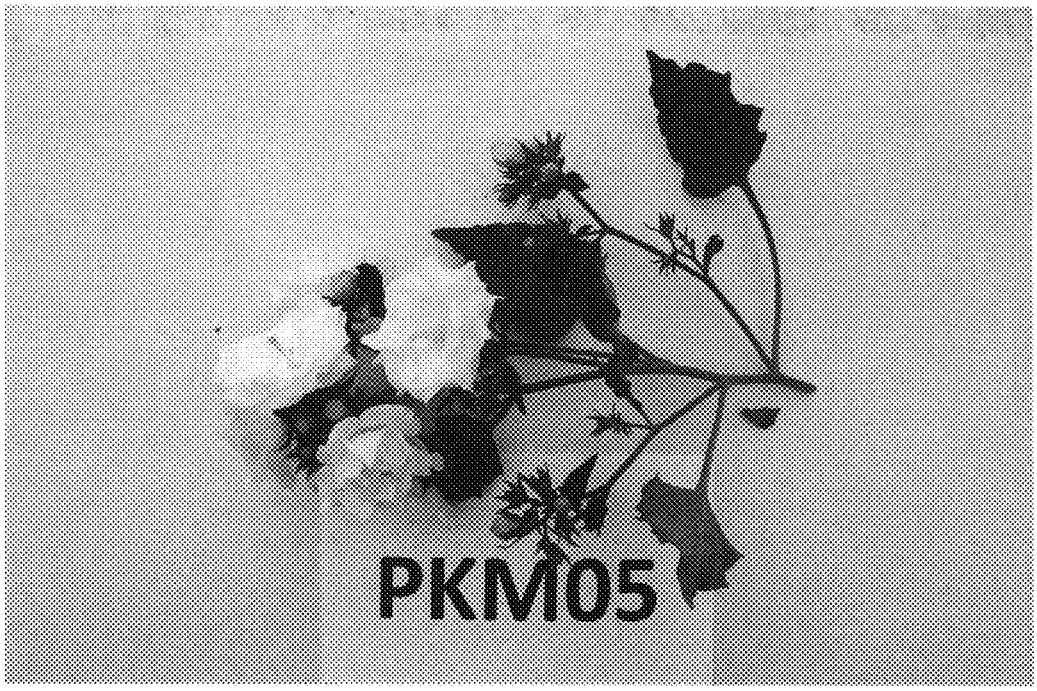

FIG. 2 comprises a close-up view of inflorescence of 'PKM05'.

Figure 3:
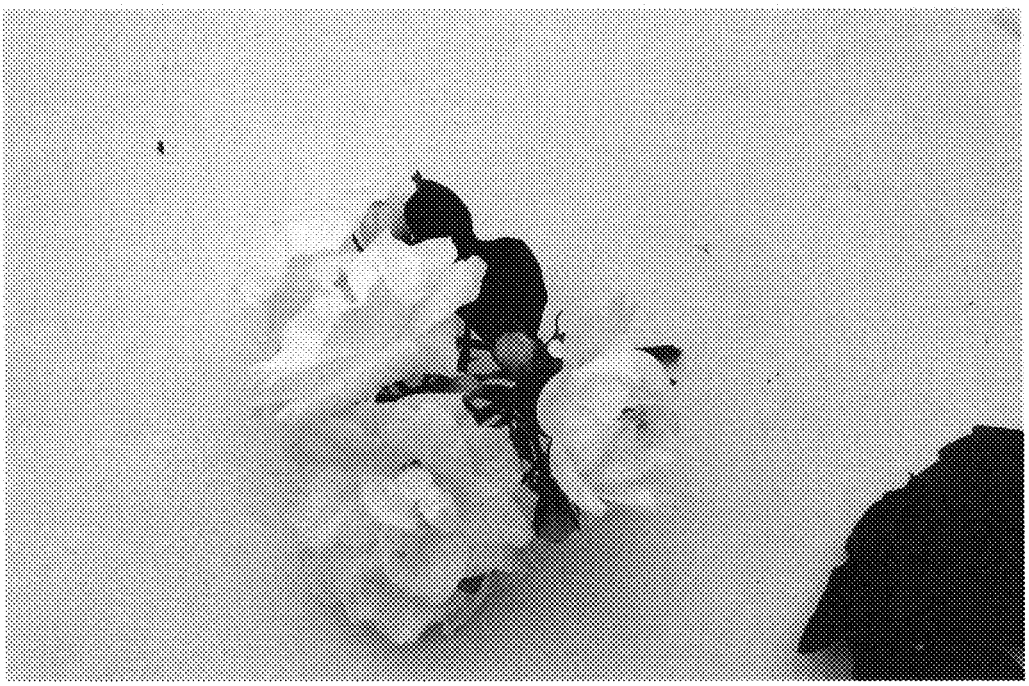

FIG. 3 comprises a close-up view of flowers of 'PKM05'.

Figure 4:
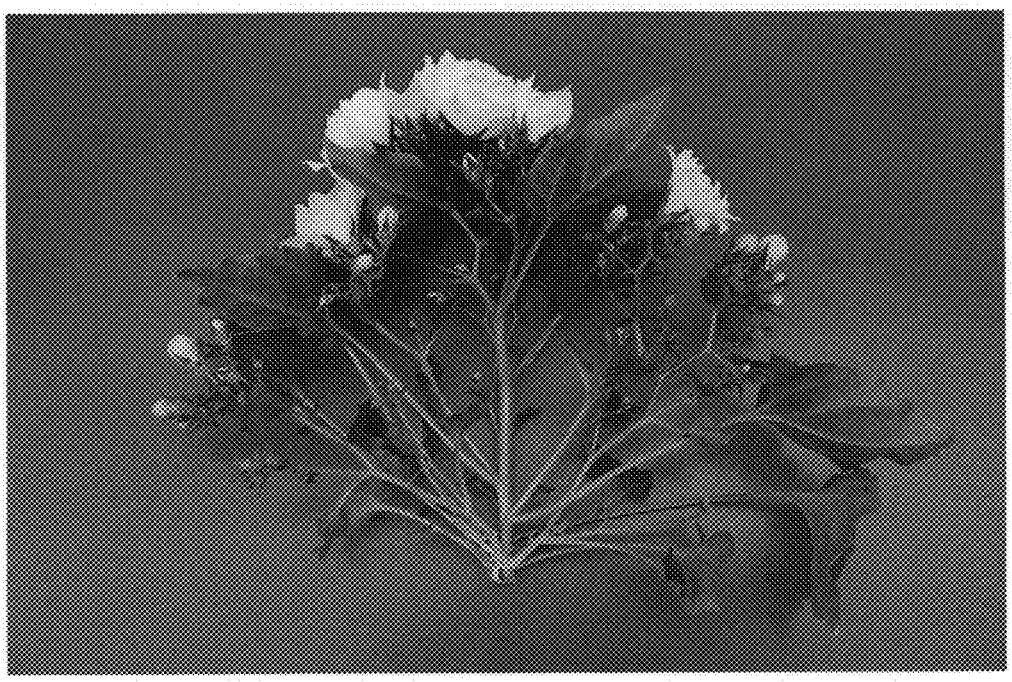

FIG. 4 comprises a close-up view of major laterals, buds, and flowers of 'PKM05'.

Figure 5:
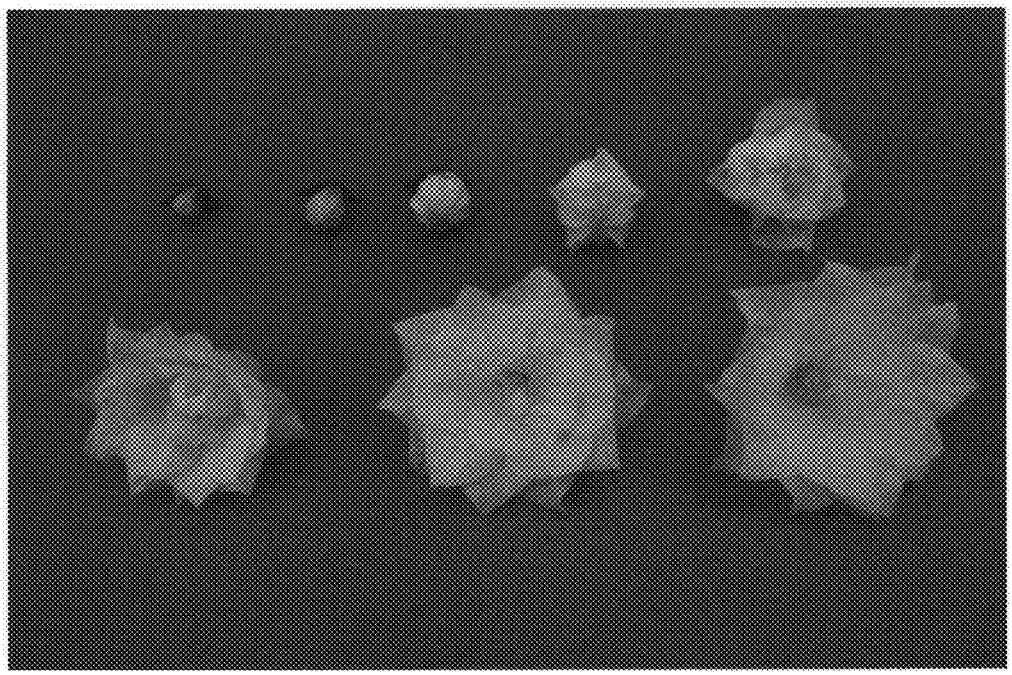

FIG. 5 comprises views of buds and flowers of 'PKM05' at various stages of opening.

DETAILED BOTANICAL DESCRIPTION

The new *Campanula* 'PKM05' has not been observed under all possible environmental conditions. The phenotype of the new cultivar may vary with variations in environment such as growth regulator treatment, temperature, light intensity, day length, and fertility level without any variance in genotype.

The aforementioned photographs, together with the following observations, measurements and values describe plants of the new *Campanula* 'PKM05' as grown under greenhouse conditions.

The age of the 'PKM05' plants described is 3 months after propagation. Color references are made to The Royal Horticultural Society Colour Chart (R.H.S.), 5$^{th}$ edition, 2007, except where general colors of ordinary significance are used.

Classification:

*Botanical.*—*Campanula* interspecific hybrid.

Parentage:

*Female or seed parent.*—*Campanula* unpatented proprietary selection.

*Male or pollen parent.*—*Campanula* unpatented proprietary selection.

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Upright plant habit. Double to filled wide campanulate flowers in panicles. Freely branching with lateral branches forming at every node.

*Crop time.*—After rooting, about 12 weeks are required to produce finished flowering plants in 10.5 cm pots.

*Plant height (from soil level to top of plant plane).*—About 18 cm. Depending on growth conditions.

*Plant spread.*—Up to 25 cm, depending on growth conditions.

*Vigor.*—Vigorous growth rate.

Lateral branches (stem):

*Length.*—Up to 20 cm.

*Internode length.*—From 1.5 to 4 cm, up to 10 nodes.

*Color.*—Between RHS 137B and 137C, green.

*Diameter.*—Up to 5 mm.

*Strength.*—Stiff.

*Lactate.*—Present.

Foliage description:

*Leaf shape.*—Single, dentate, cordate, palmate venation.

*Leaf length.*—Up to 4 cm.

*Leaf width.*—Up to 4 cm.

*Number.*—Up to 10 per lateral branch.

*Arrangement.*—Alternate.

*Apex.*—Acute.

*Base.*—Cordate.

*Margin.*—Broadly dentate, undulate.

*Texture.*—Glabrous on upper and lower surfaces; stiff.

*Color.*—Upper Surface, RHS N137A, Green. Lower Surface, between RHS 137B and 137C (Green).

*Venation color.*—Lighter green than or similar to leaf blade, but areas too small to determine R.H.S. values.

*Variegation.*—Absent.

*Petiole.*—Length: Up to 6 cm. Diameter: Up to 3 mm. Color: Between RHS 137B and 137C (green).

Inflorescence description:

*Flower arrangement and shape.*—Single, upright, double to filled flowers in panicles with many flowers at lateral branches, flowers with star shaped calyx.

*Natural flowering season.*—Continuous throughout spring and summer. Season can be extended through long day treatments, no vernalization needed.

*Flower longevity.*—Individual flowers up to three weeks. Flowers persistent.

*Inflorescence size.*—Length: up to 17 cm.

*Flowers.*—Length: About 2 cm. Diameter: About 4 cm. Layers of corollas: 3-4. Number per inflorescence: 5-8, depending on growth conditions. Shape: Wide campanulate. Fragrance: None. Petals: Number: 5, fused to form corolla. Margin: Entire. Texture: Glabrous, both upper and lower surface.

*Corolla.*—Length of tube: 20 mm. Length of lobe: 10 mm. Width of lobe: 15 mm. Tip of lobe: acute and twisted. Curvature: As flowers fill/double the curvature varies between weakly reflexing, straight, and weakly incurving.

*Corolla color.*—Upper and Lower surfaces, 155D, white.

*Petaloid lobes.*—Absent.

*Sepals.*—Arrangement: Free and sessile. Quantity per flower: 5. Length: 10 mm. Width: 3 mm. Overall shape: Triangular. Tip: Acute. Margin: Entire. Texture: Glabrous, both upper and lower surface. Color (mature and immature): Upper and lower surfaces: Green (areas too small to give R.H.S. values). Pedicel: Length: up to 7 mm. Diameter: up to 2 mm. Color: Green, RHS N137A. Buds: Shape: Obovate, pyriforme to subglobose, rosulate when opening. Color: Initially RHS 158D; RHS 155D when open.

Reproductive organs:

*Gynoecium.*—Pistil and Stigma: Shape: Tripartite, can be malformed. Color: White green tip before opening; area too small to determine R.H.S. value. Style: Color: White, RHS 155D. Length: Up to 2 cm. Ovary. Color: RHS N137A, Green.

*Androecium.*—

*Stamen.*—Often absent/malformed.

*Anther.*—Number: Up to 5. Color: Pale yellow, area too small to determine R.H.S. value. Length: 2-3 mm.

*Filaments.*—Color: White, RHS 155D. Length: Up to 12 mm.

*Pollen.*—Amount: Mostly absent. Color: Pale yellow, too scarce to determine R.H.S. value.

Temperature tolerance: Not tested.

Pest/disease tolerance: Not tested.

I claim:

1. A new and distinct cultivar of *Campanula* plant named 'PKM05', as illustrated and described herein.

* * * * *